(12) United States Patent
Vogt et al.

(10) Patent No.: US 12,343,056 B2
(45) Date of Patent: Jul. 1, 2025

(54) DEVICE FOR PROVIDING BONE CEMENT DOUGH

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 446 days.

(21) Appl. No.: 17/934,385

(22) Filed: Sep. 22, 2022

(65) Prior Publication Data

US 2023/0097874 A1 Mar. 30, 2023

(30) Foreign Application Priority Data

Sep. 28, 2021 (EP) .................................... 21199464

(51) Int. Cl.
*A61B 17/88* (2006.01)

(52) U.S. Cl.
CPC .. *A61B 17/8833* (2013.01); *A61B 2017/8838* (2013.01)

(58) Field of Classification Search
CPC ........ A61B 17/8833; A61B 2017/8838; A61B 17/88; A61B 17/8802
See application file for complete search history.

(56) References Cited

U.S. PATENT DOCUMENTS

| | | |
|---|---|---|
| 4,671,263 A | 6/1987 | Draenert |
| 4,973,168 A | 11/1990 | Chan |
| 5,100,241 A | 3/1992 | Chan |
| 5,344,232 A | 9/1994 | Nelson et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 6,709,149 B1 | 3/2004 | Tepic |

(Continued)

FOREIGN PATENT DOCUMENTS

| | | | |
|---|---|---|---|
| CA | 3056983 A1 * | 6/2020 | ......... A61B 17/8822 |
| DE | 3640279 A1 | 6/1987 | |
| DE | 69812726 T2 | 2/2004 | |

(Continued)

*Primary Examiner* — Kevin T Truong
*Assistant Examiner* — Diana Jones
(74) *Attorney, Agent, or Firm* — Dicke, Billig & Czaja, PLLC

(57) ABSTRACT

A device for providing a bone cement dough from two starting components, comprising a hollow cylindrical cartridge with an interior space, wherein a bone cement powder as the first starting component is stored in a proximal part of the interior space, and at least two pouches containing a monomer liquid as a second starting component are stored in a distal part of the interior space, wherein a dispensing plunger axially movable in the interior space is arranged between the bone cement powder and the at least two pouches, and a delivery plunger axially movable in the interior space is arranged on a side of the at least two pouches that is axially opposite the dispensing plunger, wherein the proximal part and the distal part of the interior space are fluidically connected to one another via a conduit means.

15 Claims, 10 Drawing Sheets

(56) References Cited

U.S. PATENT DOCUMENTS

2019/0380758 A1* 12/2019 Vogt .................... B01F 35/7173
2019/0380759 A1* 12/2019 Vogt .................... B01F 35/7131

FOREIGN PATENT DOCUMENTS

| DE | 102009031178 B3 | 9/2010 |
|----|----------------|--------|
| EP | 0692229 A1 | 1/1996 |
| EP | 0796653 A2 | 9/1997 |
| EP | 1005901 A2 | 6/2000 |
| EP | 1016452 A2 | 7/2000 |
| EP | 1020167 A2 | 7/2000 |
| EP | 1886647 A1 | 2/2008 |
| WO | 9426403 A1 | 11/1994 |
| WO | 9967015 A1 | 12/1999 |

* cited by examiner

DEVICE FOR PROVIDING BONE CEMENT DOUGH

CROSS-REFERENCE TO RELATED APPLICATIONS

This application claims priority pursuant to 35 U.S.C. 119 to European Application No. 21199464.5, filed Sep. 28, 2021, which application is incorporated herein by reference in its entirety.

FIELD

The invention relates to a device for providing a bone cement dough from two starting components, comprising a hollow cylindrical cartridge with an interior space, wherein a bone cement powder as the first starting component is stored in a proximal part of the interior space, and at least two pouches containing a monomer liquid as a second starting component are stored in a distal part of the interior space, wherein a dispensing plunger axially movable in the interior space is arranged between the bone cement powder and the at least two pouches, and a delivery plunger axially movable in the interior space is arranged on a side of the at least two pouches that is axially opposite the dispensing plunger, wherein the proximal part and the distal part of the interior space are fluidically connected to one another via a conduit means.

The invention further relates to a method for providing a bone cement dough from two starting components by means of such a device.

BACKGROUND OF THE INVENTION

Considerable efforts are made to demonstrate devices and methods for providing bone cement by means of which bone cement dough can be provided easily, reliably, and quickly. An important aspect in providing bone cement dough is the avoidance of air inclusions, for example gas bubbles, in the bone cement. A multitude of vacuum cementing systems in order to avoid air inclusions in the bone cement dough has been described, of which the following are cited by way of example: U.S. Pat. Nos. 6,033,105 A, 5,624,184 A, 4,671,263 A, 4,973,168 A, 5,100,241 A, WO 99/67015 A1, EP 1020167 A2, U.S. Pat. No. 5,586,821 A, EP 1016452 A2, DE 3640279 A1, WO 94/26403 A1, EP 1005901 A2, EP 1886647 A1, U.S. Pat. No. 5,344,232 A.

The desire in the market is to simplify the provision of bone cement dough. A further development exists in the development of cementing systems in which both starting components are stored in separate regions of the mixing systems and are only mixed with one another in the cementing system immediately before the cementing application. Such closed systems, what are known as full-prepacked systems, are mentioned in the following documents: EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A.

In the aforementioned full-prepacked systems, a monomer liquid is mixed with a bone cement powder via mechanical mixing, for example by means of a mixing rod.

In patent specification EP 3 320 870 B1, in contrast to the aforementioned full-prepacked systems, a device is described in which the mixing of a monomer liquid with a bone cement powder takes place only by injecting the monomer liquid into bone cement powder, in particular compacted bone cement powder. The described device therefore manages without mechanical mixing, in particular without a mixing rod. Such devices are consequently designed without a mixing apparatus.

In the device, a container filled with monomer liquid is mounted axially after a region filled with a bone cement powder within a cartridge. A dispensing plunger is arranged between bone cement powder and container. In order to provide a bone cement dough, a delivery plunger, which is arranged on a side of the container opposite the dispensing plunger, is advanced in the direction of the dispensing plunger, whereby the container is opened, in particular by partially bursting a container in the form of a glass ampule into container portions. The monomer liquid leaving the container is delivered by continually advancing the delivery plunger into the bone cement powder to form the bone cement dough. In addition to glass ampules, pouches filled with monomer liquid are also referred to as containers. In order to support the opening of the containers, in one development of the device, an opening aid can be arranged on a side of the dispensing plunger facing toward the container.

Comparable devices are also described in patent specifications EP 3 320 869 B1 and EP 3 403 716 B1.

Given these devices, the amount of bone cement powder and monomer liquid are coordinated with one another so that the monomer liquid is sufficient to completely wet the bone cement powder. An incomplete wetting would have negative effects on the quality and homogeneity of the bone cement dough.

However, there are limitations involved in using pouches as containers for the monomer liquid. These pouches are usually made of multi-layer composite films with an EVOH barrier layer, optionally comprising a metal coating, in particular comprising an aluminum coating, wherein transport regulations mean that a pouch may only be filled with up to 30 ml of monomer liquid. If larger amounts of bone cement dough are to be provided, it may therefore be necessary to use two or more pouches which are respectively filled with up to 30 ml of monomer liquid.

For production reasons, all pouches filled with monomer liquid always have a gas inclusion, for example air or a protective gas, in particular nitrogen or argon. The gas included in the pouches must be transferred through the bone cement powder, which is in particular compacted, before the bone cement powder comes into contact with the monomer liquid to form the bone cement dough. A contacting of the bone cement dough being formed with the gas included in the pouches would otherwise lead to air inclusions, for example gas bubbles, in the bone cement dough, which, due to the lack of mechanical mixing, could no longer be removed from said bone cement dough before dispensing from the device. Gas bubbles in the bone cement dough have negative effects on the mechanical properties of the bone cement produced from the bone cement dough by curing, which has a disadvantageous effect on the stability of a joint endoprosthesis fixed therewith.

Patent specifications EP 3 320 870 B1, EP 3 320 869 B1, and EP 3 403 716 B1 do not disclose how two or more pouches are to be opened without the bone cement dough provided containing air inclusions, such as gas bubbles.

OBJECTS

It is an object of the present invention to at least partially overcome one or more of the disadvantages resulting from the prior art.

The invention is especially based on the goal of providing a device which can provide even larger amounts of bone cement dough easily, reliably, quickly, and without gas bubbles, in particular using two or more pouches filled with monomer liquid. The device should provide the bone cement without a mechanical mixing of the starting components. The device should furthermore be designed such that the user does not need to implement any assembly steps. The device should be capable of providing the bone cement without an externally applied vacuum. The device should be able to dispense the provided bone cement. The device should be able to dispense the provided bone cement without modification measures. The device should provide and dispense the bone cement without modification measures and without external equipment such as, for example, hoses, vacuum sources, or extrusion devices. The device should be able to be operated with as few work steps as possible, in order to minimize error sources by the user.

It is a further object of the invention to provide a method with which bone cement can be provided from two starting components, by means of which at least some of the objects already described are at least partially achieved.

PREFERRED EMBODIMENTS OF THE INVENTION

A contribution to at least partial fulfillment of at least one of the aforementioned objects is achieved via the features of the independent claims. The dependent claims provide preferred embodiments that contribute to at least partially fulfillment of at least one of the objects.

A first embodiment of the invention is a device for providing a bone cement dough from two starting components, comprising a hollow cylindrical cartridge with an interior space, wherein a bone cement powder as the first starting component is stored in a proximal part of the interior space, and at least two pouches containing a monomer liquid as a second starting component are stored in a distal part of the interior space, wherein a dispensing plunger axially movable in the interior space is arranged between the bone cement powder and the at least two pouches, and a delivery plunger axially movable in the interior space is arranged on a side of the at least two pouches that is axially opposite the dispensing plunger, wherein the proximal part and the distal part of the interior space are fluidically connected to one another via a conduit means, characterized in that the dispensing plunger can be subdivided into four equal-sized quadrants on a distal side of the dispensing plunger facing toward the at least two pouches, wherein each of the four quadrants has at least one opening means so that, by advancing the delivery plunger in the direction of the dispensing plunger, the at least two pouches are to be opened, in particular concertedly opened, by the opening means, and the monomer liquid is to be delivered into the bone cement powder.

In one embodiment of the device, the opening means comprise a tip, a cutting edge, or a tip and a cutting edge to open the pouches. This embodiment is a second embodiment of the invention, which is preferably dependent on the first embodiment of the invention.

In one embodiment of the device, the opening means are spaced apart from a longitudinal axis of the dispensing plunger at a distance in a range of one-fifth, as a fraction ⅕, up to four-fifths, as a fraction ⅘, of a radius of the distal side of the dispensing plunger. This embodiment is a third embodiment of the invention, which is preferably dependent on the first or second embodiment of the invention.

In one embodiment of the device, the opening means comprise in each quadrant, in particular in each individual quadrant, at least one inner opening means and at least one outer opening means, wherein the respective inner opening means and the respective outer opening means are arranged in each quadrant concentrically about the longitudinal axis of the dispensing plunger. This embodiment is a fourth embodiment of the invention, which is preferably dependent on the third embodiment of the invention.

In one embodiment of the device, the opening means comprise a metal, a polymer, or a combination of the aforementioned. In particular, the cone segments consist of a polymer or a metal or a combination of the aforementioned. This embodiment is a fifth embodiment of the invention, which is preferably dependent on one of the preceding embodiments of the invention.

In one embodiment of the device, the conduit means comprise in each quadrant, in particular in each individual quadrant, at least one fluid-conducting feedthrough extending axially through the dispensing plunger in order to fluidically connect the proximal part and the distal part of the interior space to one another. This embodiment is a sixth embodiment of the invention, which is preferably dependent on one of the preceding embodiments of the invention.

In one embodiment of the device, the feedthroughs open on the distal side of the dispensing plunger into a groove extending, in particular extending superficially, in the distal side of the dispensing plunger, which groove fluidically connects the feedthroughs to one another.

This embodiment is a seventh embodiment of the invention, which is preferably dependent on the sixth embodiment of the invention.

In one embodiment of the device, the feedthroughs in each individual quadrant comprise at least one inner feedthrough and one outer feedthrough, wherein the inner feedthroughs lead into an inner groove extending, in particular extending superficially, in the distal side of the dispensing plunger, and the outer feedthroughs open into an outer groove extending, in particular extending superficially, in the distal side of the dispensing plunger, wherein the inner groove fluidically connects the inner feedthroughs to one another and the outer groove fluidically connects the outer feedthroughs to one another. This embodiment is an eighth embodiment of the invention, which is preferably dependent on the sixth embodiment of the invention.

In one embodiment of the device, the inner groove and the outer groove are fluidically connected to one another via a connecting groove extending, in particular extending superficially, in the distal side of the dispensing plunger. This embodiment is a ninth embodiment of the invention, which is preferably dependent on the eighth embodiment of the invention.

In one embodiment of the device, the delivery plunger has a receptacle, on a proximal side of the delivery plunger facing toward the dispensing plunger, in order to receive the opening means when the delivery plunger is advanced in the direction of the dispensing plunger. This embodiment of the invention is a tenth embodiment of the invention, which is preferably dependent on one of the preceding embodiments of the invention.

In one embodiment of the device, the receptacle comprises recesses in order to receive the opening means when the delivery plunger is advanced in the direction of the dispensing plunger. This embodiment of the invention is an eleventh embodiment of the invention, which is preferably dependent on the tenth embodiment of the invention.

In one embodiment of the device, the receptacle comprises an elastomer layer in order to receive the opening means when the delivery plunger is advanced in the direction of the dispensing plunger. This embodiment is a twelfth embodiment of the invention, which is preferably dependent on the tenth embodiment of the invention.

A thirteenth embodiment of the invention is a method for providing a bone cement dough from two starting components by means of a device according to any one of the preceding embodiments, comprising the following steps:
 a. advancing the delivery plunger in the direction of the dispensing plunger while opening the at least two pouches via the opening means,
 b. delivering the monomer liquid into the proximal part of the interior space while forming the bone cement dough.

In one embodiment of the method, the device is inserted into a dispensing apparatus to advance the delivery plunger. This embodiment is a fourteenth embodiment of the invention, which is preferably dependent on the thirteenth embodiment of the invention.

In one embodiment of the method, the monomer liquid is distributed in the bone cement powder with the aid of a hydrophilic additive. This embodiment is a fifteenth embodiment of the invention, which is preferably dependent on the thirteenth or fourteenth embodiment of the invention.

GENERAL

In the present description, range information also includes the values specified as limits. A specification of the type "in the range of X to Y" with respect to a variable A consequently means that A can assume the values X, Y, and values between X and Y. Ranges delimited at one end of the type "up to Y" for a variable A correspond accordingly to a value Y and less than Y.

Some of the described features are linked to the term "substantially." The term "substantially" is to be understood as meaning that, under real conditions and manufacturing techniques, a mathematically exact interpretation of concepts such as "superimposition," "perpendicular," "diameter" or "parallelism" can never apply exactly, but can only apply within certain manufacturing-related error tolerances. For example, "substantially perpendicular axes" include an angle of 85 degrees to 95 degrees relative to one another, and "substantially equal volumes" include a deviation of up to 5% by volume. A "device consisting substantially of plastic" comprises, for example, a plastic fraction of ≥95 to ≤100% by weight. A "substantially complete filling of a volume B" comprises, for example, a filling of ≥95 to ≤100% by volume of the total volume of B.

The terms "proximal" and "distal" merely serve to designate the spatially opposite ends of the device, or of other structural units of the device, and do not allow any conclusions to be drawn about the orientation in relation to a human body, for example of a user of the device. "Distal to . . . " and "proximal to . . . " or similar formulations accordingly express only the spatial arrangement of two structural units of the device relative to one another.

DETAILED DESCRIPTION

A first subject matter of the invention relates to a device for providing a bone cement dough from two starting components, comprising a hollow cylindrical cartridge with an interior space, wherein a bone cement powder as the first starting component is stored in a proximal part of the interior space, and at least two pouches containing a monomer liquid as a second starting component are stored in a distal part of the interior space, wherein a dispensing plunger axially movable in the interior space is arranged between the bone cement powder and the at least two pouches, and a delivery plunger axially movable in the interior space is arranged on a side of the at least two pouches that is axially opposite the dispensing plunger, wherein the proximal part and the distal part of the interior space are fluidically connected to one another via a conduit means, characterized in that the dispensing plunger can be subdivided into four equal-sized quadrants on a distal side of the dispensing plunger facing toward the at least two pouches, wherein each of the four quadrants has at least one opening means so that, by advancing the delivery plunger in the direction of the dispensing plunger, the at least two pouches are to be opened, in particular concertedly opened, by the opening means, and the monomer liquid is to be delivered into the bone cement powder.

The distal side of the dispensing plunger facing the at least two pouches has at least one opening means in each of its equal-sized quadrants. The device, in particular the distal side of the dispensing plunger, thus has at least four opening means which are arranged such that the at least two pouches are to be opened reliably and concertedly, i.e. synchronously, in particular substantially simultaneously, by pushing the pouches against the opening means. This enables a concerted escape of the gas located in the pouches, which, together with a gas already present in the distal part of the interior space before the pouch is opened, can be transferred, by continued advancing of the delivery plunger in the direction of the dispensing plunger, via the conduit means and through the bone cement powder, before the monomer liquid stored in the pouches is delivered into the bone cement powder via the conduit means to form the bone cement dough. This makes it possible to provide a bone cement dough without gas bubbles. If, on the other hand, the pouches were to be opened in a highly chronologically staggered manner, the risk would be that the formation of the bone cement dough would already begin before the last pouch were opened, so that gas located in the last pouch would lead to air inclusions, for example gas bubbles, in the bone cement dough as it forms.

At least two pouches containing a monomer liquid are stored within the distal part of the interior space of the device. A pouch is understood to mean a non-rigid, optimally flexible storage option which can store the monomer liquid in a hermetically tight and sterile manner and can be opened by means of the action of an opening means, for example by piercing, cutting open, or tearing open. The pouches can, for example, be manufactured from a multilayer composite film, preferably comprising an EVOH barrier layer. Optionally, the pouches can have a metal coating, in particular an aluminum coating.

In order to ensure a reliable and concerted opening of the at least two pouches, it is preferred that the pouches are arranged next to one another, at the same distance from the opening means, in the distal part of the interior space so that, by advancing the delivery plunger in the direction of the dispensing plunger, the pouches can be pushed concertedly, in particular substantially simultaneously, against the opening means.

Pouches filled with monomer liquid are often not spherical, but rather are of elongate shape with a longitudinal axis of the pouch. In order to push the at least two pouches concertedly against the opening means and to open them in this way, in particular to open them concertedly, it is preferred to arrange the pouches next to one another in such a way that the longitudinal axes of the pouches extend substantially parallel to a longitudinal axis of the dispensing plunger in the distal part of the interior space.

An opening means is understood to mean a structural unit or structural sub-unit formed on the distal side of the dispensing plunger, which unit can open a pouch, in particular pierce it, cut it open, or tear it open when the opening means and the pouch are pushed against one another. In order to facilitate the opening, in particular attaching, cutting open, or tearing open, it is preferred that the opening means can be pressed against the pouches with a surface area that is small in comparison to a cross-sectional area of the interior space; the opening means are thus "sharp" and/or "pointed" in the broadest sense.

Depending on the nature of the pouch and the opening means, a differing application of force can be necessary to open the pouch by means of the opening means. In particular, the application of force by the opening means is reduced in comparison to an application of force required when opening the pouches by means of two planar plungers.

In order to open the pouches reliably and in a controlled and concerted manner, the opening means have an axial extension in the direction of the delivery plunger, which extension has, for example, a value in a range from 5 mm to 15 mm, preferably 5 mm to 10 mm, more preferably 6 mm to 8 mm. In one embodiment of the device, opening means having the described axial extension additionally function as a spacer for opened pouches with respect to the conduit means, so that a risk of the conduit means being blocked by the opened pouches or pouch sections is reduced.

The device has a hollow cylindrical cartridge. A hollow cylindrical cartridge is to be understood as a tubular receptacle which has an interior space and a cartridge wall surrounding the interior space. The cross-section of the cartridge can take any shape. Due to the simple manufacture and the application-safe use of the device, the cross section and preferably also the cross section of the interior space, is circular. This allows an ease of handling for the user, and the absence of edges reduces the risk of movable parts wedging within the device. According to the invention, the cartridge can consist of a wide variety of materials or material combinations. Examples the device can consist of a polymer. The polymer is preferably a transparent polymer, since the user can, in this way, optically monitor a proper functioning of the device during use.

A dispensing plunger, which is axially movable in the interior space, is arranged between the bone cement powder and the container. The dispensing plunger serves to spatially separate the at least two pouches and the bone cement powder so that cement powder from the proximal part of the interior space can neither pass into the distal part of the interior space, nor can the pouches pass from the distal part of the interior space into the proximal part of the interior space. In particular, the latter prevents a bone cement dough which is permeated by pouches or pouch sections, which could represent health risks to the patient and could impair proper dispensing of the bone cement dough from the device. The dispensing plunger furthermore serves to dispense the provided bone cement dough from the device. For this purpose, the dispensing plunger can be moved out of its original position in the direction of a dispensing opening of the device. The dispensing opening is preferably located on a side of the bone cement powder that is axially opposite the dispensing plunger. In order to remove gas, in particular gas stored in the pouches, from the device, in particular before the bone cement dough is formed, it is preferred that the dispensing opening be designed to be gas permeable. For example, the dispensing opening can be closed with a gas-conducting closure, such as a plug, for example, which can be removed from the dispensing opening for dispensing the mixed bone cement dough.

The device has a delivery plunger that is axially movable in the interior space. The delivery plunger is arranged within the device on the side of the pouches that is axially opposite the dispensing plunger. Via an advancement, i.e. via a relative movement of the delivery plunger in the direction of the dispensing plunger, which shortens the distance of delivery plunger and dispensing plunger within the interior space, the pouches are opened by the opening means.

A continued advancement of the delivery plunger in the direction of the dispensing plunger results in the monomer liquid leaving the pouches being delivered, via the conduit means, from the distal part of the interior space of the device into the proximal part of the interior space of the device. This results in bone cement powder and monomer liquid being brought into contact to form a bone cement dough.

The device has a conduit means via which the distal part and the proximal part of the interior space are fluidically connected. Fluidically means that the distal part and the proximal part of the interior space are connected in a manner that is permeable to liquids, in particular the monomer liquid, and to gases. In order to prevent bone cement powder from being able to pass from the proximal part into the distal part of the interior space and the at least two pouches, in particular pouch sections, from being able to arrive from the distal part into the proximal part of the interior space via the conduit means, the conduit means is preferably equipped with a filter means, in particular a porous disk, made for example of sintered polypropylene particles; of sintered or compressed polyethylene fibers; of cellulose felt; or of cardboard, which renders the conduit means impermeable to solids. In a variant of the device, at least one channel is provided in the dispensing plunger and/or between the dispensing plunger and the inner wall of the interior space as a conduit means, via which the distal part and the proximal part of the interior space are fluidically connected to one another. A filter, for example a porous disk, made for example of sintered polypropylene particles; of sintered or compressed polyethylene fibers; of cellulose felt; or of cardboard, which is impermeable to the bone cement powder and is permeable to the monomer liquid and gases, can thereby be arranged in or at one or both ends of the at least one channel. In a further variant of the device, the conduit means is one or more conduits which is or are arranged on the outside of the cartridge or in the cartridge wall and connects or connect the distal part and the proximal part of the interior space. The dispensing plunger is bypassed in this variant.

By advancing the delivery plunger in the direction of the dispensing plunger, it is achieved that the monomer liquid can be transferred within the interior space of the cartridge via the conduit means, from the distal part of the interior space into the proximal part of the interior space in which the bone cement powder is located.

A variant of the device is designed such that a continuous advancement of the delivery plunger in the direction of the dispensing plunger, after the monomer liquid has been conveyed from the distal part of the interior space into the proximal part of the interior space, causes the dispensing plunger to advance in the direction of the dispensing opening of the device. In this way, the bone cement dough provided by mixing bone cement powder and monomer liquid can be discharged from the device through the discharge opening. It is herewith achieved in a simple manner that the bone cement dough is to be expelled from the cartridge with the same actuation which is also used to open the pouches and to deliver the monomer liquid, namely with the unidirectionally driven delivery plunger.

In order to prevent an unintentional advancement of the dispensing plunger in the direction of the dispensing opening, a catch means can be arranged on the dispensing plunger so that the dispensing plunger can engage with the cartridge, in particular with the cartridge wall, between the proximal part and the distal part of the interior space, wherein this detent is not to be released by the forces occurring upon opening of the pouches and a pressure exerted on the monomer liquid by the delivery plunger during the conveying of the monomer liquid into the proximal part of the interior space, but can be released by a direct pressure of the delivery plunger and any pouches or pouch sections located therebetween on the dispensing plunger or on the opening means.

Via the catch means, it is achieved that the pouches can first be opened by advancing the delivery plunger, and the monomer liquid leaving from there can subsequently be pressed with the dispensing plunger into the proximal part of the interior space of the cartridge, i.e. into the bone cement powder, wherein the dispensing plunger thereby maintains its original position relative to the cartridge and to the interior space. Only after the monomer liquid has been largely pressed into the bone cement powder, and thus the bone cement dough is present in the proximal part of the interior space of the cartridge, can the bone cement dough subsequently be pressed with the dispensing plunger out of the proximal part of the cartridge. The force for releasing the detent is therefore greater than the force required to open the pouches and to deliver the monomer liquid via the conduit means into the proximal part of the interior space.

In order to prevent an unintentional opening of the pouches, for example upon transport of the device, it may be preferred that a transport locking device is arranged in the distal part of the interior space, between the opening means and the pouches. The transport locking device can be formed, for example, from a plate with perforations for the subsequent permeation of the opening means, which plate is spaced apart on the distal side of the dispensing plunger by means of webs which bend when the force is applied.

It can also be provided that the device has a means for pressure relief with which excess, pressurized monomer liquid can be discharged after the transfer of the monomer liquid into the bone cement powder.

In order to enable a concerted, substantially simultaneous opening of the pouches, all pouches should be pushed against the opening means in a concerted, substantially simultaneous manner. To this end, at least one of the opening means is arranged on the distal side of the dispensing plunger, in each of the four quadrants of the distal side of the dispensing plunger.

The four quadrants of the distal side of the dispensing plunger are all the same size and together form the complete distal side of the dispensing plunger. There is no region of the distal side of the dispensing plunger facing toward the pouches which cannot be associated with one of the quadrants.

The number and arrangement of the opening means according to the claim ensures that the pouches can be opened reliably and concertedly, substantially simultaneously.

It is thereby preferred that the pouches are arranged next to one another and parallel to the longitudinal axis of the dispensing plunger and have a substantially equal-sized axial extension in the distal part of the interior space.

The opening means can be formed differently in order to open the pouches.

One embodiment of the device is characterized in that the opening means comprises a tip, in particular a needle-like tip; a cutting edge or a tip, in particular a needle-like tip; and a cutting edge. The cutting edge can thereby be designed as a straight line and/or curved, for example in the shape of a circular arc. The cutting edge can, for example, thereby have a length in a range from 1 mm to 8 mm.

In one embodiment, the individual opening means are designed to be disjoint from one another, except for their connection via the imaginary planar distal side of the dispensing plunger. In a further embodiment, the opening means are part of a common structure, for example as tips of a sawtoothed structural elevation of the distal side of the dispensing plunger.

The opening means and the distal side of the dispensing plunger can be designed as one piece or integrally. One piece means that the opening means and the distal side of the dispensing plunger are composed of individual components. Integrally means that the opening means are shapings of the distal side of the dispensing plunger.

Within the quadrants, the opening means can be arranged at different positions in order to ensure reliable and concerted opening of the pouches.

One embodiment of the device is characterized in that the opening means are spaced apart from the longitudinal axis of the dispensing plunger at a distance in a range of one-fifth up to four-fifths of a radius of the dispensing plunger. In this embodiment, the opening means have a distance from the longitudinal axis of the dispensing plunger which corresponds to 0.2 times to 0.8 times the radius of the distal side of the dispensing plunger. In a preferred embodiment, the dispensing plunger has a substantially circular cross section, so that the longitudinal axis of the dispensing plunger travels through the center point of the cross section and through the contact point of all four quadrants. The radius of the distal side of the dispensing plunger corresponds to a distance from the center point of the distal side of the dispensing plunger to an edge of the distal side of the dispensing plunger. At most, an opening means could be removed at a distance from the longitudinal axis of the dispensing plunger which corresponds to the radius of the distal side of the dispensing plunger. In order to ensure a reliable and concerted opening of the pouches, the opening means are removed from the longitudinal axis with a distance which corresponds to 0.2 times to 0.8 times the radius of the distal side of the dispensing plunger.

In one embodiment of the device, all opening means have the same distance from the longitudinal axis of the dispensing plunger. In this embodiment, the opening means are arranged concentrically about the longitudinal axis of the dispensing plunger.

Each quadrant can have a plurality of opening means.

One embodiment of the device is characterized in that the opening means comprise at least one inner opening means and at least one outer opening means in each quadrant. Therefore, at least two opening means are present in each quadrant. The inner opening means thereby have a smaller distance from the longitudinal axis of the dispensing plunger than the outer opening means. The inner opening means and the outer opening means preferably respectively have the same distance from the longitudinal axis of the dispensing plunger. In this preferred embodiment, the inner opening means and the outer opening means are thus respectively arranged concentrically about the longitudinal axis of the dispensing plunger.

The opening means can comprise different materials or consist of different materials.

One embodiment of the device is characterized in that the opening means comprise a metal, a polymer, or a combination of a metal and a polymer, in particular consist of a metal, a polymer, or a metal and a polymer. Examples of metals are titanium, tantalum, aluminum, iron, and steel, in particular stainless steel. Examples of polymers are polyamides, polyamide-imides, polyaryl ethers, polysulfones, polyether ketones. The polymers should thereby be mechanically durable in such a way that opening of the pouches is reliably achieved.

The conduit means can be designed in different ways in order to reliably fluidically connect the distal part and the proximal part of the interior space, particularly also after the opening of the pouches.

Since the pouches are compressed, after the opening and in the course of the delivery of the monomer liquid from the distal part into the proximal part of the interior space, by advancing the delivery plunger in the direction of the dispensing plunger, there is a risk of the conduit means being blocked by a pouch, in particular by an opened pouch or a pouch section. A blocked conduit means is fluidically closed or is only slightly fluidically opened, such that the monomer liquid can only be delivered into the bone cement powder very slowly, for example not within one minute.

One embodiment of the device is therefore characterized in that the conduit means comprises in each quadrant at least one fluid-conducting feedthrough, extending axially through the dispensing plunger, in order to fluidically connect the distal part and the proximal part of the interior space. The at least four feedthroughs run from the distal side of the dispensing plunger to a proximal side of the dispensing plunger, which is axially opposite the distal side of the dispensing plunger, through the dispensing plunger. Since at least one feedthrough is present in each quadrant, the risk of a complete blockage resulting from all feedthroughs of the conduit means being blocked simultaneously by the pouches, in particular by an opened pouch or a pouch section, is reduced.

Analogous to the description of the conduit means, fluidically means that the distal part and the proximal part of the interior space are connected in a manner that is permeable to liquids, in particular the monomer liquid, and to gases. In order to prevent bone cement powder from being able to pass from the proximal part into the distal part of the interior space, and the at least two pouches from being able to pass from the distal part into the proximal part of the interior space via the conduit means, the feedthroughs are preferably equipped with a filter means, in particular a porous disk, made for example of sintered polypropylene particles, of sintered or compressed polyethylene fibers, of cellulose felt, or of cardboard, which renders the feedthroughs impermeable to solids.

In one embodiment, the feedthroughs all have the same distance from the longitudinal axis of the dispensing plunger.

In order to be able to deliver the monomer liquid virtually completely and reliably into the proximal part of the interior space even given partial blockage of the conduit means, for example given blockage of one or two feedthroughs in one or two quadrants, in one embodiment the feedthroughs are fluidically connected to one another on the distal side of the dispensing plunger. In this way, the monomer liquid can be guided reliably from a blocked feedthrough to a feedthrough that is fluidically open.

One embodiment of the device is characterized in that the feedthroughs on the distal side of the dispensing plunger open into a groove running in the distal side of the dispensing plunger, which groove fluidically connects the feedthroughs to one another. A groove is a depression, in particular a depression that is semicircular or rectangular in cross section, in the distal side of the dispensing plunger, through which the monomer liquid can flow from a feedthrough to a further feedthrough in another quadrant. It is thereby preferred that the groove is designed to be circular in plan view, so that the monomer liquid can be guided from a blocked feedthrough in two different directions to further feedthroughs. The groove preferably has a groove width in a range of 1 mm to 3 mm, so that the risk of the groove being blocked by a pouch, in particular by an opened pouch or a pouch section, is reduced.

In one embodiment, the feedthroughs all have the same distance from the longitudinal axis of the dispensing plunger, and the groove is circular and configured concentrically about the longitudinal axis of the dispensing plunger.

More than one feedthrough can be arranged in each quadrant of the distal side of the dispensing plunger.

One embodiment of the device is characterized in that the feedthroughs in each quadrant comprise at least one inner feedthrough and an outer feedthrough, wherein the inner feedthrough has a smaller distance from the longitudinal axis of the dispensing plunger than the outer feedthrough.

The respective inner feedthroughs and the respective outer feedthroughs are preferably fluidically connected to one another. For this purpose, the inner feedthroughs open into an inner groove running in the distal side of the dispensing plunger, and the outer feedthroughs open into an outer groove running in the distal side of the dispensing plunger.

It is thereby preferred that the inner groove and the outer groove are respectively circular in plan view of the distal side of the dispensing plunger, so that the monomer liquid can be guided from a blocked feedthrough in two different directions to further feedthroughs. The inner groove and the outer groove preferably have a groove width in a range of 1 mm to 3 mm, so that the risk of the grooves being blocked by a pouch, in particular by an opened pouch or a pouch section, is reduced.

In one embodiment, the respective inner feedthroughs and the respective outer feedthroughs have the same distance from the longitudinal axis of the dispensing plunger, and the inner groove and the outer groove are respectively circular and designed concentrically about the longitudinal axis of the dispensing plunger.

In order to further reduce the risk of the conduit means being blocked, an embodiment of the device is characterized in that the inner groove and the outer groove are fluidically connected to one another at least via a connecting groove running in the distal side of the dispensing plunger. The inner groove and the outer groove can, for example, be fluidically connected to one another via two, three, four, or more connecting grooves.

The connecting groove preferably has a groove width in a range of 0.5 mm to 3 mm, so that the risk of the connecting groove being blocked by a pouch, in particular by an opened pouch or a pouch section, is reduced.

One embodiment of the device is characterized in that the delivery plunger has a receptacle on a proximal side of the delivery plunger facing toward the dispensing plunger, in order to receive the opening means upon advancing the delivery plunger in the direction of the dispensing plunger. The receptacle allows the opening means to be accommodated in the delivery plungers, so that the dispensing plunger and the delivery plunger can be pushed closer together than without the receptacle. Without the receptacle, the dispensing plunger and the delivery plunger would be spaced apart by the opening means. The receptacle thus allows better utilization of the monomer liquid, which is present in the pouches, for providing the bone cement dough.

The receptacle can be designed differently in order to receive the opening means into the delivery plunger.

One embodiment of the device is characterized in that the receptacle comprises recesses, preferably that the receptacle consists of recesses. The recesses represent depressions in the proximal side of the conveying plunger, into which the opening means can be inserted. Preferably, the recesses are designed such that the opening means substantially completely fill the recesses. In this preferred embodiment, the recesses represent a negative form of the opening means.

One embodiment of the device is characterized in that the receptacle comprises an elastomer layer, preferably that the receptacle consists of an elastomer layer. The elastomer layer is thereby elastic, so that the opening means compress the elastomer layer in portions upon advancing the delivery plunger in the direction of the dispensing plunger, and the non-compressed portions of the elastomer layer fill an intermediate space between the opening means as completely as possible in order to deliver the monomer liquid as completely as possible into the proximal part of the interior space.

A further subject matter of the invention relates to a method for providing a bone cement dough from two starting components by means of a device, in particular by means of a device according to one of the preceding embodiments, comprising the following steps:
 a. advancing the delivery plunger in the direction of the dispensing plunger while opening the at least two pouches via the opening means,
 b. delivering the monomer liquid into the proximal part of the interior space to form the bone cement dough.

By advancing the delivery plunger, the pouches are pressed against the opening means until, in the course of the advancement, the pouch is opened by the opening means, in particular by piercing, cutting open, or tearing open. The monomer liquid which thereupon escapes from the pouches can subsequently be delivered into the proximal part of the interior space. The gas also leaving the pouches, together with the gas already present in the distal part of the internal space before the pouch is opened, can already be delivered chronologically before the monomer liquid via the conduit means and through the bone cement powder, so that no gas connections occur during the formation of the bone cement dough chronologically thereafter. In order to first deliver the gas and then the monomer liquid via the conduit means into the proximal part of the interior space, the device is preferably held during delivery in such a way that the proximal part of the interior space is held spatially higher than the distal part of the interior space. As a result, the gas collects spatially above the monomer liquid and is conveyed, in front of the monomer liquid, via the conduit means in the direction of the dispensing plunger given a continued advancement of the delivery plunger.

The delivery plunger can be advanced in different ways into the cartridge, in the direction of the dispensing plunger. For example, a user of the device can advance the delivery plunger manually, in particular via the application of force to a rod or axle. In a further embodiment, the cartridge and the delivery plunger together form a thread via which the delivery plunger can be screwed into the cartridge in the direction of the dispensing plunger. The cartridge thereby preferably has an internal thread and the delivery plunger has an external thread, which interact in a form-fitting and/or force-fitting manner in order to enable the advancement of the delivery plunger.

In one embodiment of the method, the delivery plunger is advanced using a mechanical aid.

One embodiment of the method is characterized in that, in order for the delivery plunger to be advanced, the device is inserted into a dispensing device, in particular an applicator gun for bone cement dough. Applicator guns for bone cement dough are known to the person skilled in the art.

The formation of the bone cement dough from the two starting components begins with the delivery of the monomer liquid from the distal part into the proximal part of the interior space. This preferably takes place with the most uniform possible mixing of the two starting components, in order to obtain as homogeneous a bone cement dough as possible. The two components can be mixed in different ways. In one embodiment of the method, the mixing takes place with the active cooperation of the user of the device, for example with shaking of the device or by actuating a mixing element, in particular a stirrer, in the proximal part of the interior space.

One embodiment of the method is characterized in that the monomer liquid is distributed in the bone cement powder with the aid of a hydrophilic additive. One advantage is that this takes place without active involvement of the user of the device, which avoids possible user errors in the mixing. One possible error is that the user does not mix over the entire length of the proximal part of the interior space, so that parts of the bone cement powder are not wetted with monomer liquid. A further advantage is that the device can thereby be designed more simply and with fewer moving components, which reduces both the risk of malfunctions and the production costs of the device.

The device is characterized in that it provides a bone cement dough from two starting components. Bone cement dough is understood to mean a substance which is suitable in the field of medical technology for creating a stable connection between artificial joints, such as hip and knee joints, and bone material. A bone cement is produced from a bone cement dough via curing. These bone cements are preferably polymethyl methacrylate bone cements. PMMA bone cements have already been used in medical applications for a long time and date back to work by Sir Charnley. PMMA bone cements can thereby be produced from a bone cement powder as a first starting component and a monomer liquid as a second starting component. Given a suitable composition, the two starting components can be stable when stored separately from one another. Upon bringing the two starting components into contact, a plastically deformable bone cement dough is produced by swelling of the polymer components of the bone cement powder. A polymerization of the monomer is thereby initiated by radicals. With progressing polymerization of the monomer, the viscosity of the bone cement dough increases until it is completely cured.

Bone cement powder is understood to mean a powder which comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive which supports the distribution of the monomer liquid within the bone cement powder. In a further embodiment, the bone cement powder can additionally comprise an initiator which starts the polymerization. In a further embodiment, the bone cement powder can additionally comprise a radioopacifier. In yet a further embodiment, the bone cement powder can additionally comprise pharmaceutically active substances such as, for example, antibiotics.

The bone cement powder preferably comprises, as a hydrophilic additive, at least one particulate polymethyl methacrylate and/or a particulate polymethyl methacrylate copolymer, an initiator, and a radioopacifier, or consists of said components. Further preferably, the bone cement powder comprises at least one particulate polymethyl methacrylate and/or a particulate polymethyl methacrylate copolymer, an initiator, a radioopacifier, and a hydrophilic additive, or consists of said components. Most preferably, the bone cement powder comprises at least one particulate polymethyl methacrylate and/or a particulate polymethyl methacrylate copolymer, an initiator, a radioopacifier, a hydrophilic additive, and an antibiotic, or consists of said components.

According to the invention, the particle size of the particulate polymethyl methacrylate and/or the particulate polymethylmethacrylate copolymer of the bone cement powder of the sieve fraction can correspond to less than 150 µm, preferably less than 100 µm.

According to the invention, the hydrophilic additive can be embodied in particulate and/or fibrous form. In a further embodiment, the hydrophilic additive can be sparingly soluble, preferably insoluble, in methyl methacrylate. In a further embodiment, the hydrophilic additive can have an absorbency capacity of at least 0.6 g methyl methacrylate per gram of hydrophilic additive. In a further embodiment, the hydrophilic additive can have a chemical substance with at least one OH group. It can thereby preferably be provided that the hydrophilic additive has covalently bonded OH groups on its surface. Examples of such preferred hydrophilic additives can be additives selected from the group comprising cellulose, oxycellulose, starch, titanium dioxide, and silicon dioxide, wherein pyrogenic silicon dioxide is particularly preferred. In one embodiment, the particle size of the hydrophilic additive of the sieve fraction can correspond to less than 100 µm, preferably less than 50 µm, and most preferably less than 10 µm. The hydrophilic additive can be contained in an amount of 0.1 to 2.5% by weight, relative to the total weight of the bone cement powder.

According to the invention, the initiator can contain dibenzoyl peroxide or consist of dibenzoyl peroxide.

According to the invention, a radioopacifier is understood to mean a substance which makes it possible to render the bone cement visible in diagnostic x-ray exposures. Examples of radioopacifiers may include barium sulfate, zirconium dioxide, and calcium carbonate.

According to the invention, the pharmaceutically active substance can comprise one or more antibiotics, and optionally added co-factors for the one or more antibiotics. The pharmaceutically active substance preferably consists of one or more antibiotics, and optionally added co-factors for the one or more antibiotics. Examples of antibiotics are, among other things, gentamicin, clindamycin, and vancomycin.

According to the invention, the monomer liquid can comprise methyl methacrylate or consist of methyl methacrylate. In one embodiment, in addition to the monomer, the monomer liquid comprises an activator dissolved therein such as, for example, N,N-dimethyl-p-toluidine, or consists of methyl methacrylate and N,N-dimethyl-p-toluidine.

The features disclosed for the device are also disclosed for the method, and vice versa.

FIGURES

The invention is illustrated by way of example below by means of Figures. The invention is not limited to the Figures.

The following are shown:

FIG. 1 a schematic longitudinal section of a device for providing a bone cement dough, comprising two pouches containing a monomer liquid, FIG. 2 a schematic longitudinal section of a dispensing plunger from the device of FIG. 1, in a perspective side view, FIG. 3 a perspective side view of the dispensing plunger from FIGS. 1 and 2, FIG. 4 a plan view of a proximal side of a dispensing plunger of the dispensing plunger from FIGS. 1 to 3, FIG. 5 a plan view of a distal side of the dispensing plunger of the dispensing plunger from FIGS. 1 to 4, FIG. 6 a schematic longitudinal section of the device from FIG. 1, after the pouch has been opened, FIG. 7 a schematic longitudinal section of the device from FIGS. 1 and 6, upon formation of the bone cement dough, FIG. 8 a schematic longitudinal section of the device from FIGS. 1, 6, and 7, upon dispensing the bone cement dough, FIG. 9 a schematic longitudinal section of the device from FIGS. 1 and 6 to 8, with a dispensing device, and FIG. 10 a flow chart of a method for providing a bone cement dough.

Figure 1:
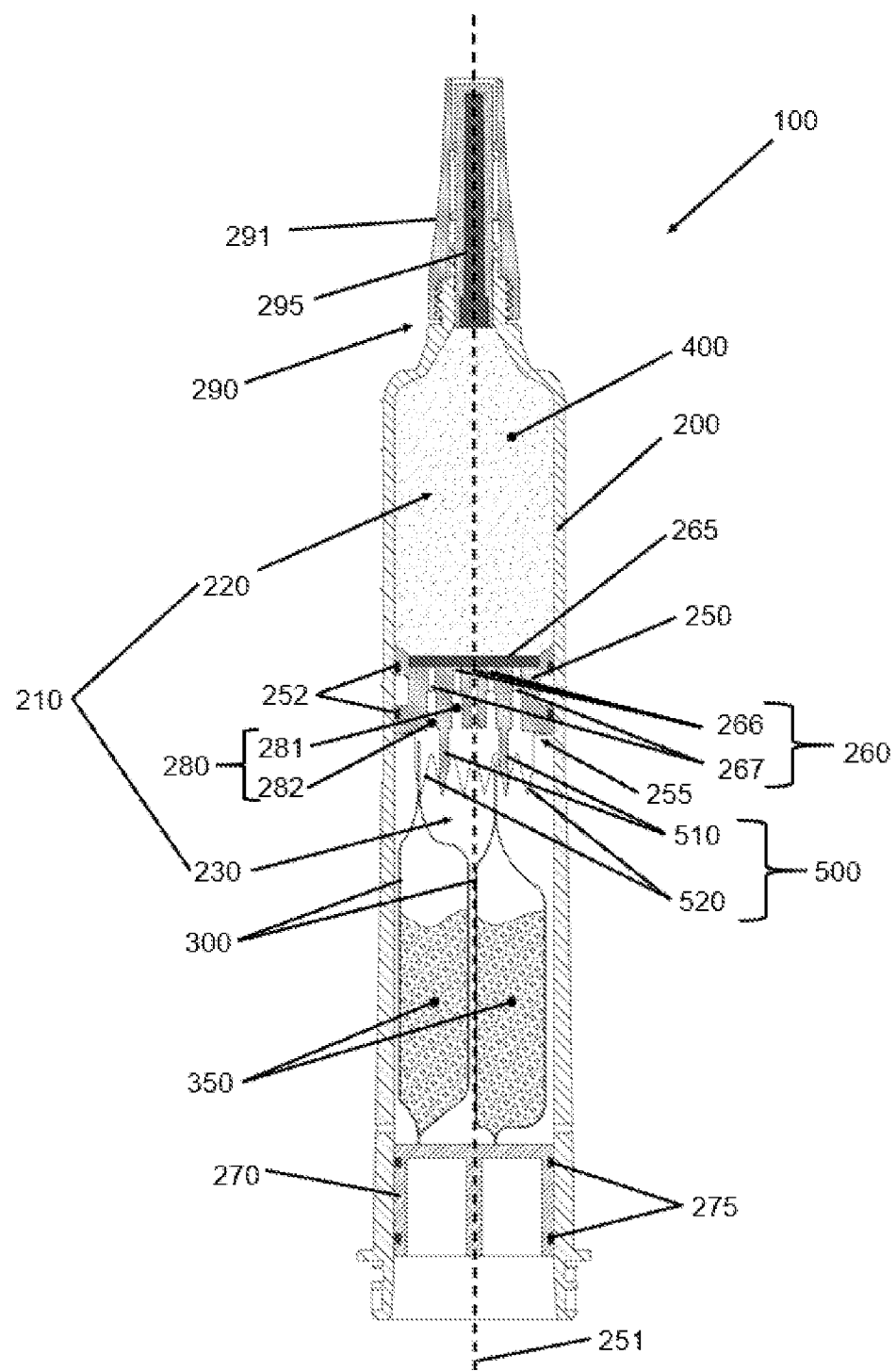
FIG. 1 shows a schematic longitudinal section of an exemplary embodiment of a device 100 for providing a bone cement dough in an initial state. The device 100 is constructed in one piece, but from a plurality of components. The device 100 is constructed in a tubular manner and comprises a hollow cylindrical cartridge 200 with an interior space 210. A bone cement powder 400 as a first starting component is stored in a proximal part 220 of the interior space 210, and two pouches 300 containing a monomer liquid 350 as a second starting component of the bone cement dough are stored in a distal part 230 of the interior space 210. For production reasons, a gas is stored in the pouches 300 in addition to the monomer liquid 350. The bone cement powder 400 contains particulate polymethyl methacrylate as a main component, and a hydrophilic additive with which the monomer liquid 350 can be distributed in the bone cement powder 400 without a mixing device.

The proximal part 220 and the distal part 230 of the interior space 210 are separated by a dispensing plunger 250 which is axially movable in the interior space 210. The dispensing plunger 250 is configured to be impermeable to solids so that no bone cement powder 400 can pass from the proximal part 210 into the distal part 230 of the interior space 210, and the pouches 300 do not pass from the distal part 230 into the proximal part 220 of the interior space 210.

The dispensing plunger 250 has a conduit means 260 in the form of a plurality of feedthroughs through which a fluid-conducting connection is formed between the proximal part 220 and the distal part 230 of the interior space 210. The conduit means 260 comprises inner feedthroughs 266 and outer feedthroughs 267, wherein the inner feedthroughs 266 have a smaller distance from a longitudinal axis 251 of the dispensing plunger 250 than the outer feedthroughs 267.

The inner feedthroughs 266 and the outer feedthroughs 267 open, on a distal side 255 of the dispensing plunger of the dispensing plunger 250 facing toward the pouches 300, into circular grooves 280 extending concentrically about the longitudinal axis 251 of the dispensing plunger 250, wherein the inner feedthroughs 266 feed into an inner groove 281 and the outer feedthroughs 267 feed into an outer groove 282. The grooves 280 fluidically connect the respective feedthroughs to one another so that the monomer liquid 350 can flow from a feedthrough which is blocked by the pouches 300 after they have been opened to a feedthrough which is fluidically open.

The conduit means 260 is closed impermeably to solids or bone cement dough by a porous disk 265, wherein the porous disk allows the monomer liquid 350 to be easily delivered out of the distal part 230 into the proximal part 220 of the interior space 210. In the shown embodiment of the device 100, the porous disk 265 is arranged on the end of the conduit means 260 facing toward the proximal part 220 of the interior space 210. In further embodiments, the porous disk 265 or another type of means is arranged on the end of the conduit means 260 facing toward the distal part 230, or on both ends of the conduit means 260. One advantage of a porous disk 265 arranged as shown is that the bone cement dough forming in the proximal part 220 of the interior space 210 cannot block the conduit means 260.

Opening means 500 for opening the pouches 300 are arranged on the distal side 255 of the dispensing plunger of the dispensing plunger 250. The opening means 250 comprise inner opening means 510 and outer opening means 520, so that the pouches 300 can be opened reliably and concertedly. For this purpose, the pouches 300 are arranged next to one another in the distal part 230 of the interior space 210 and along the longitudinal axis 251 of the dispensing plunger 250, so that both pouches 300 can be pressed concertedly against the opening means 250.

A delivery plunger 270 which is axially movable within the interior space 210 is arranged on the side of the pouches 300 opposite the dispensing plunger 250. The delivery plunger 270 closes a back side of the interior space 210 of the cartridge 200.

In order that monomer liquid 350 which has left the pouches 300 is not pressed past the dispensing plunger 250 into the proximal part 220 of the interior space 210, two radially circumferential sealing rings 252 made of rubber are provided on the dispensing plunger 250, with which the dispensing plunger 250 is sealed against the wall of the interior space 210. Likewise, two radially circumferential sealing rings 275 are provided on the delivery plunger 270, by means of which sealing rings the monomer liquid 350 is prevented from leaving the device 100 past the delivery plunger 270. The sealing effect of the sealing rings 275 on the delivery plunger 270 must be able to withstand a pressure which is exerted by the delivery plunger 270 on the monomer liquid 250 in order to deliver the monomer liquid 350, after the pouches 300 have been opened, from the distal part 230 into the proximal part 220 of the interior space 210 via the conduit means 260 and the porous disk 265.

The device 100 further comprises a dispensing opening 290 which delimits the region of the proximal part 220 of the interior space 210 of the cartridge 200 facing away from the dispensing plunger 250. In the initial state of the device 100, the dispensing opening 290 is closed by a closure cap 291 with a plug 295, so that no bone cement powder 400 can escape from the cartridge 200. The plug 295 is designed to be permeable to gas in order to be able to transfer a gas, which escapes from the pouches 300 after the pouches 300 have been opened and which is already present in the distal part 230 of the interior space before the pouches 300 are opened, through the bone cement powder 400 and out of the device 100 before the formation of the bone cement dough begins.

Figure 2:
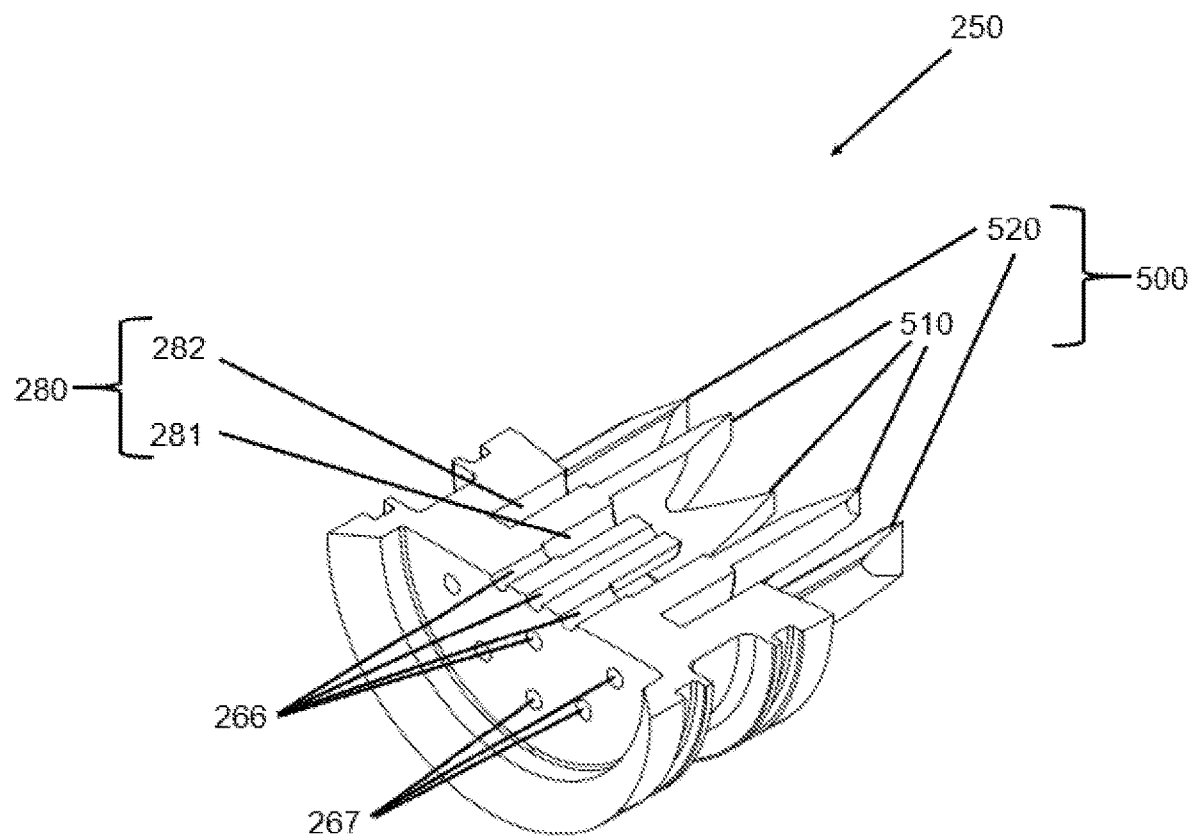

FIG. 2 shows the longitudinal section of the dispensing plunger 250 of the device 100 from FIG. 1, in a perspective side view. To avoid repetition, reference is made to the above description of FIG. 1. FIG. 2 shows that the opening means 500 comprise a cutting edge and/or a tip in order to open the pouches 300 of FIG. 1, in particular to open the pouches 300 of FIG. 1 by piercing and/or cutting open.

Figure 3:
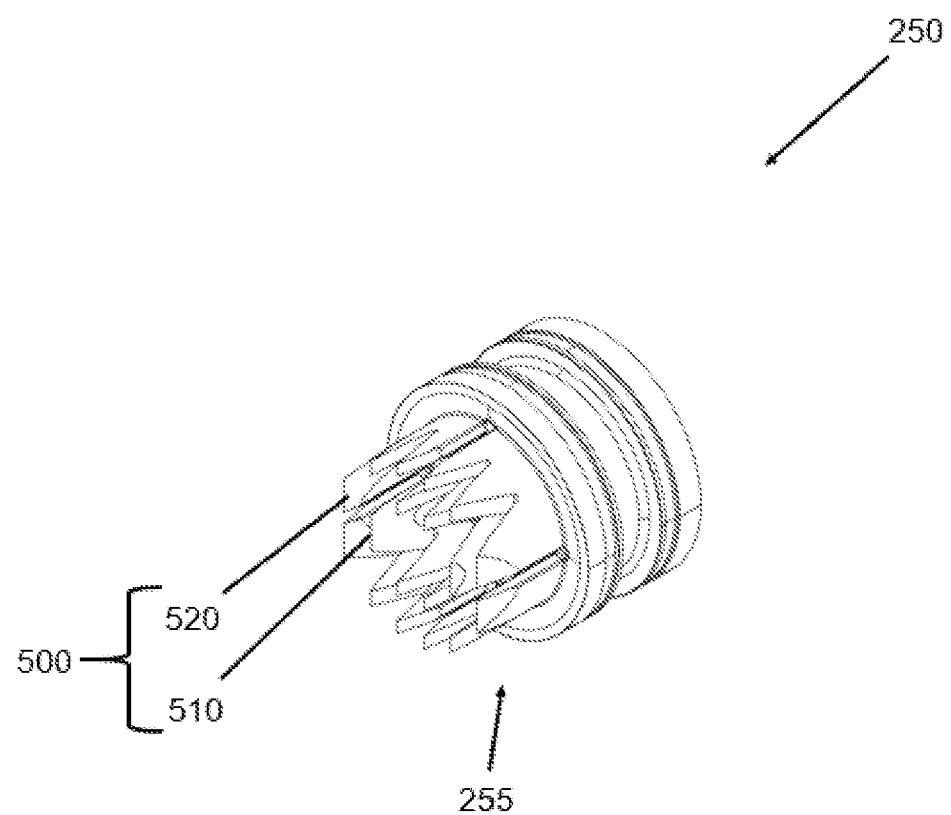

FIG. 3 shows the dispensing plunger 250 of FIGS. 1 and 2 in a further perspective side view. FIG. 3 shows that the dispensing plunger 250 has a substantially circular distal side 255 of the dispensing plunger, which can be divided into four quadrants of equal size. In each quadrant, a plurality of inner opening means 510 and outer opening means 520 are provided, which together form the opening means 500 of the dispensing plunger 250.

Figure 4:
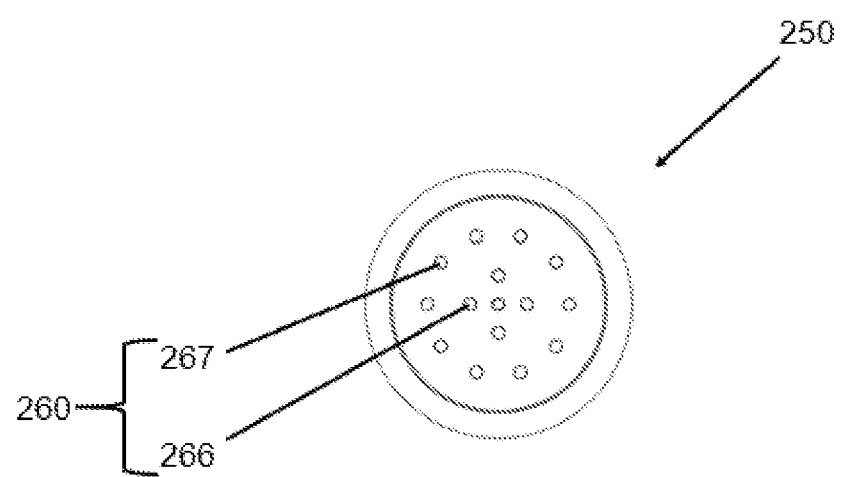

FIG. 4 shows the dispensing plunger 250 of FIGS. 1 to 3 in plan view of a proximal side of the dispensing plunger. In the device 100 of FIG. 1, the proximal side of the dispensing plunger of the dispensing plunger 250 faces toward the bone cement powder 400. It can be seen in FIG. 4 that the conduit means 260 comprise a plurality of inner feedthroughs 266 and a plurality of outer feedthroughs 267 in each quadrant of the dispensing plunger 250, so that the monomer liquid 350 of FIG. 1 can be delivered safely and reliably from the distal side 255 of the dispensing plunger onto the proximal side of the dispensing plunger. The inner opening means 266 and the outer feedthroughs 267 are respectively arranged concentrically about the longitudinal axis of the dispensing plunger 250.

Figure 5:
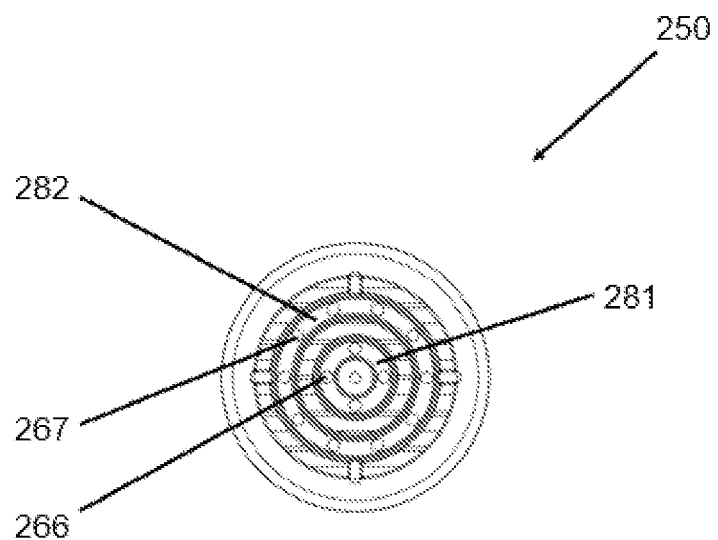

FIG. 5 shows the dispensing plunger 250 of FIGS. 1 to 4 in a plan view of the distal side of the dispensing plunger 250. The inner feedthroughs 266 open into the circular groove 281, which is concentric about the longitudinal axis of the dispensing plunger 250 and fluidically connects the inner feedthroughs 266 to one another. The outer feedthroughs 267 open into the circular outer groove 282, which is concentric about the longitudinal axis of the dispensing plunger 250 and fluidically connects the outer feedthroughs 267 to one another.

Figure 6:
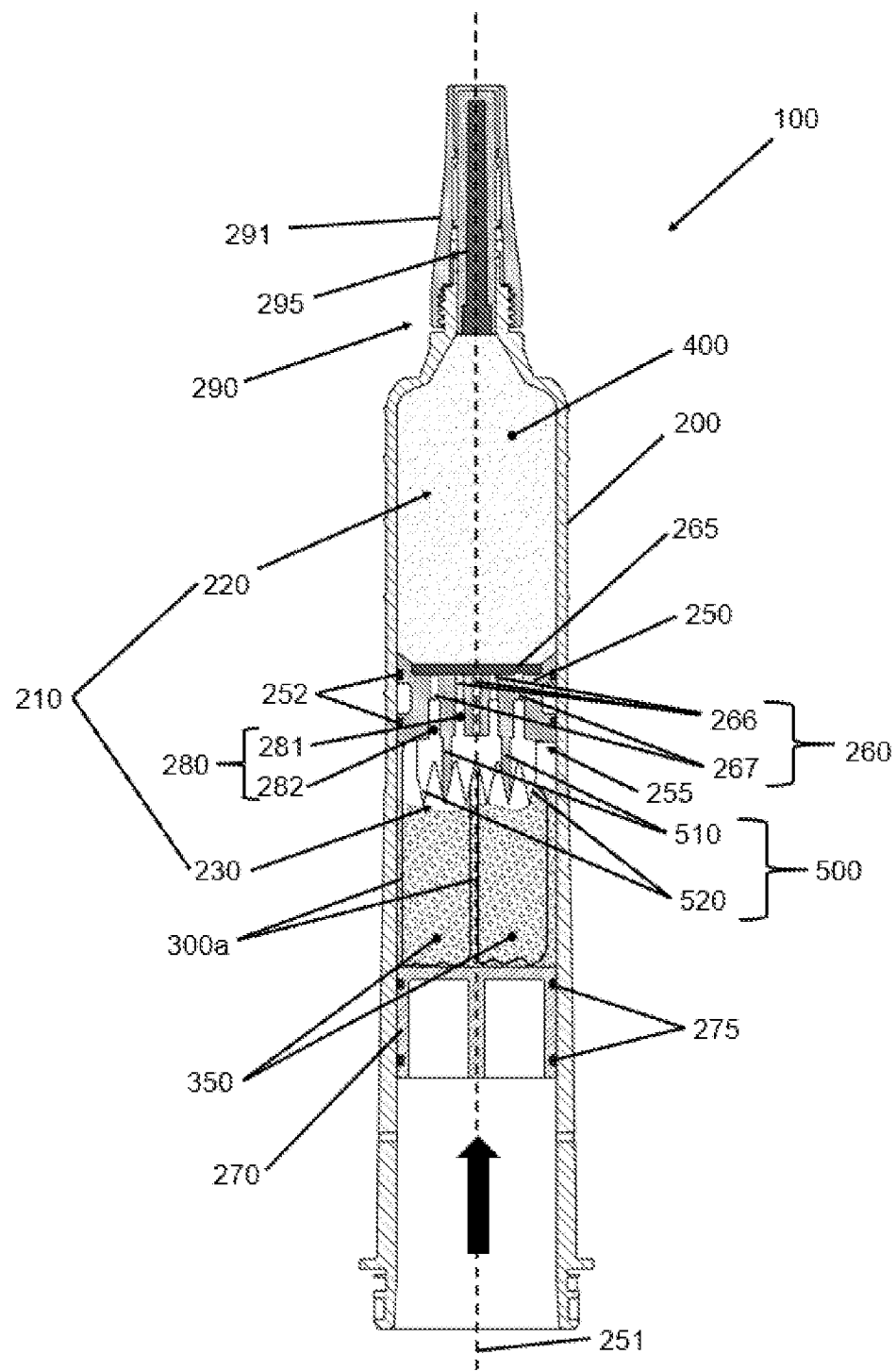

FIG. 6 shows the device 100 of FIG. 1, wherein, compared to FIG. 1, the delivery plunger 270 is advanced in the direction of the dispensing plunger 250. By advancing the delivery plunger 270, the pouches 300 of FIG. 1 were opened by the opening means 500, whereby the monomer liquid 350 flowed partially from the opened pouches 300a into the distal part 230 of the interior space 210. The gas emerging from the opened pouches 300a in the distal part 230 of the interior space 210 has, with the gas already present before the pouch 300 is opened in the distal part 230 of the interior space 210, already been transferred out of the device 100 via the conduit means 260 by advancing the delivery plunger 270 in the direction of the dispensing plunger 250, through the bone cement powder 450 and the plug 295. Due to the special embodiment and arrangement of the opening means 500, both pouches 300 of FIG. 1 were opened reliably and concertedly, substantially simultaneously. This allows an almost complete removal of the gas present in the distal part 230 of the interior space 210, before delivery of the monomer liquid 350 into the bone cement powder 400 via the conduit means 260 is started by continued advancement of the delivery plunger 270 in the direction of the dispensing plunger 250. This prevents gas bubbles in the bone cement dough as it forms. In order to first deliver the gas and then the monomer liquid 350 into the proximal part 220 of the interior space 210, the device 100 is preferably held during delivery in such a way that the proximal part 220 is held spatially higher than the distal part 230 of the interior space 210.

The advancement of the delivery plunger 270 can be accomplished in different ways. For example, to this end the device 100 can be inserted into a dispensing apparatus, which spends the delivery plunger 270 in the direction of the dispensing plunger 250 by means of a tappet.

Figure 7:
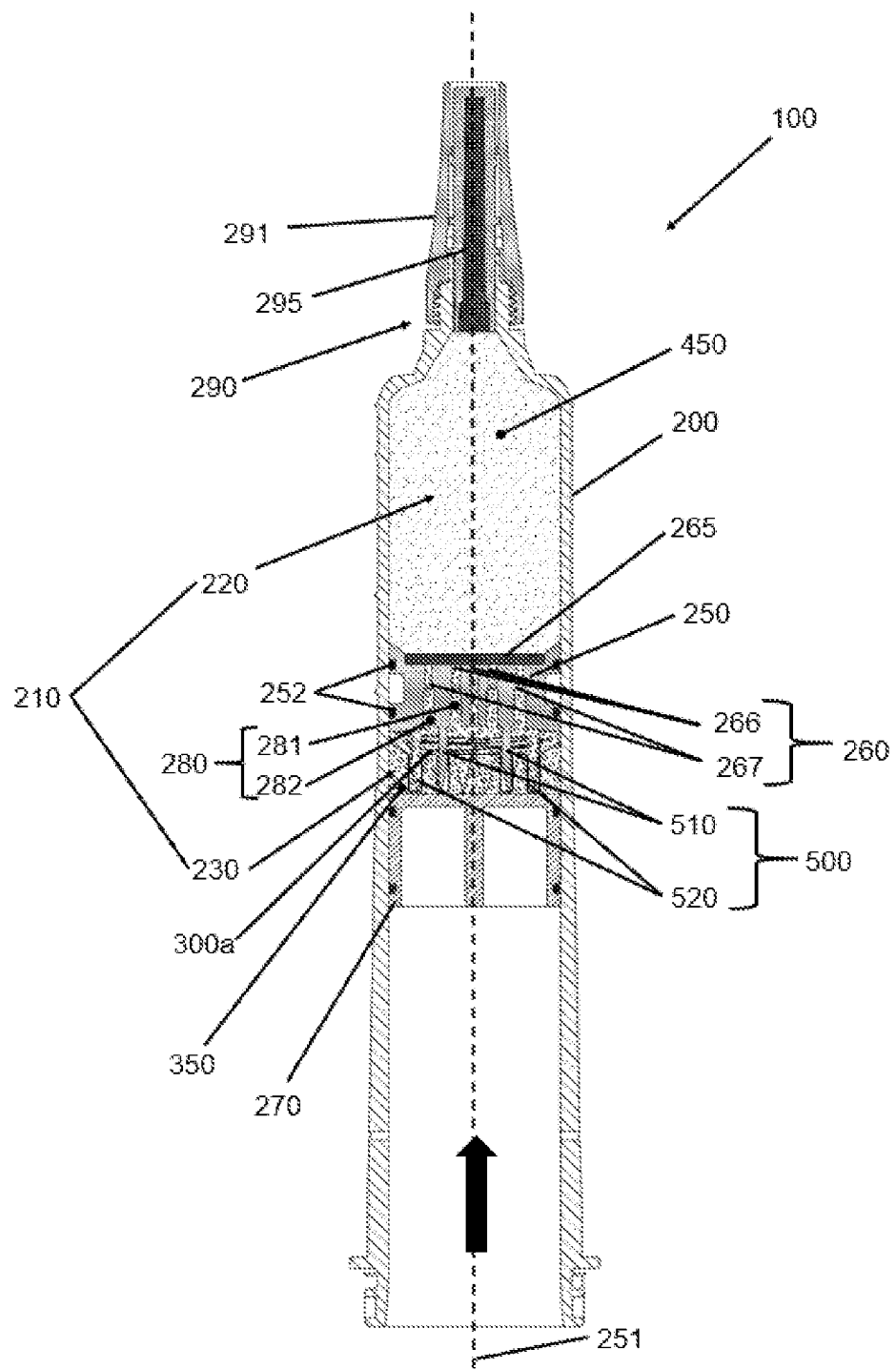

FIG. 7 shows the device 100 of FIGS. 1 and 6, wherein the delivery plunger 270 is advanced further in the direction of the dispensing plunger 250 in comparison to FIG. 6. The delivery plunger 270 is advanced so far in the direction of the dispensing plunger 250 that the delivery plunger 270 is in contact with the opening means 500. Via the advancement, the gas previously present in the distal part 230 of the interior space 210 has been substantially completely transported out of the device 100 through the conduit means 260 into the proximal part 220 of the interior space 210, and/or partially through the plug 295. Furthermore, the monomer liquid 350, except for a small fraction in an intermediate space of the opening means and in the grooves 280 and the conduit means 260, has been delivered, chronologically after the gas, via the conduit means 260 into the proximal part 220 of the interior space 210. Via the delivery, a substantially bubble-free bone cement dough 450 has been formed from the bone cement powder 400 of FIGS. 1 and 6 and the monomer liquid 350.

Via the contact of the delivery plunger 270 with the opening means 500, the delivery plunger 270 cannot be advanced further in the direction of the dispensing plunger 250 without the dispensing plunger 250 also being displaced in the direction of the dispensing opening 290. In a further embodiment of the device 100, the delivery plunger 270 comprises a receptacle which allows insertion of the opening means 500 into the delivery plunger 270. Via the receptacle, further monomer liquid 350 mounted between the dispensing plunger 250 and the delivery plunger 270 could be delivered into the proximal part 220 of the interior space 230 before an advancement of the dispensing plunger 250 starts by advancing the delivery plunger 270.

Figure 8:
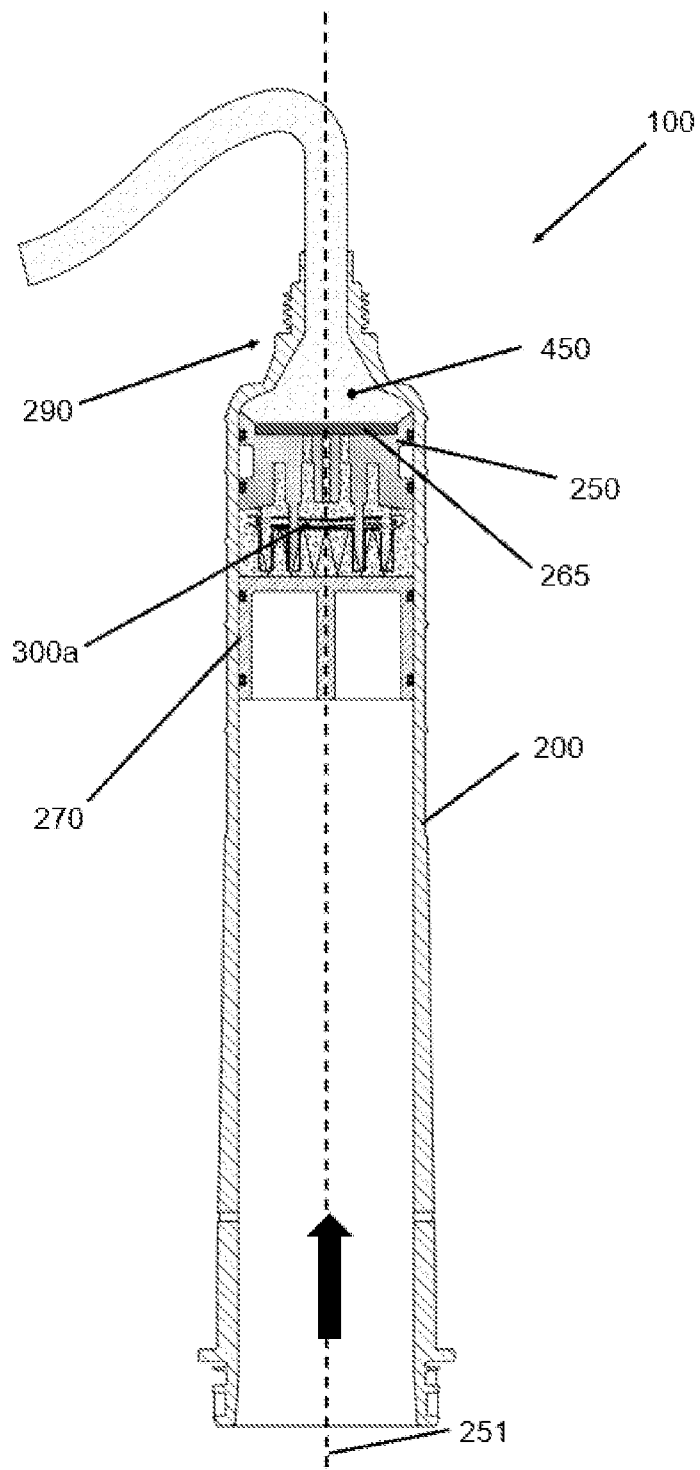

FIG. 8 shows the device 100 of FIGS. 1, 6, and 7, wherein the closure cap 291 and the plug 295 have been removed, and the delivery plunger 270, and thus also the dispensing plunger 250, are advanced further in the direction of the dispensing opening 290 as compared to FIG. 7. By advancing the dispensing plunger 250, the provided bone cement dough 450 was partially discharged from the device 100. In a further embodiment of the device 100, the dispensing opening 290 is fluidically connected to a dispensing spout which enables a targeted application of the bone cement dough 450 at a desired location.

Figure 9:
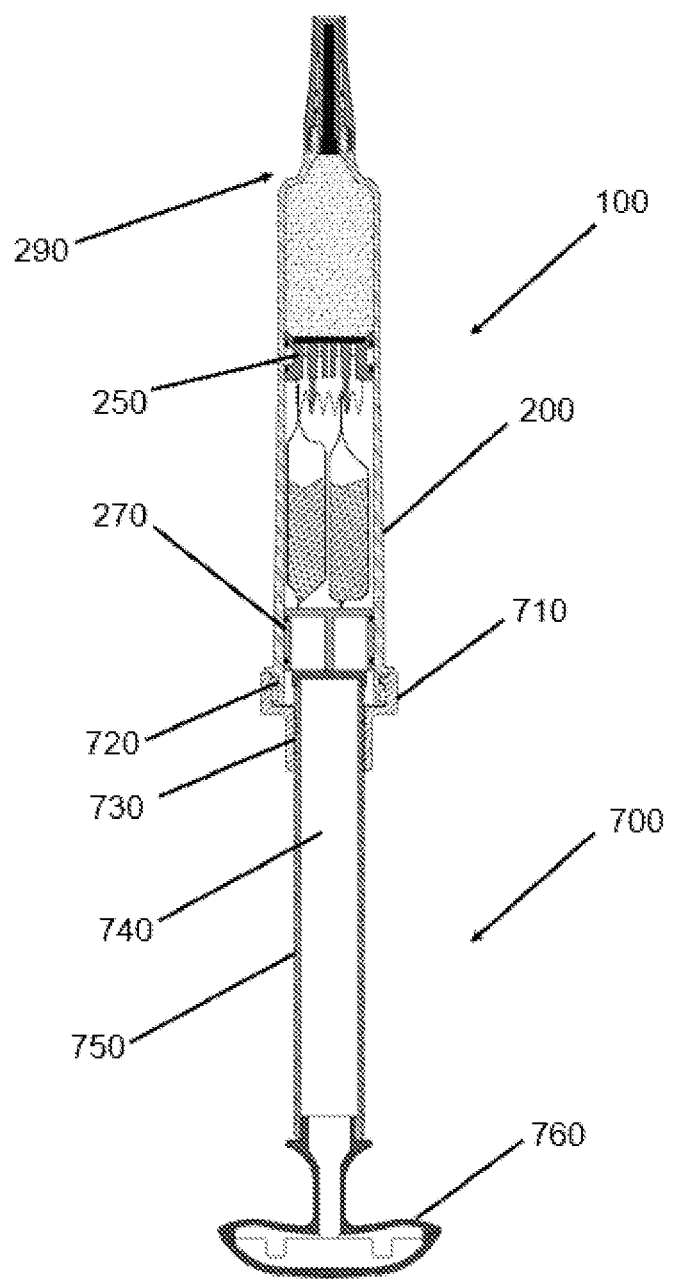

FIG. 9 shows the device 100 of FIGS. 1 and 6 to 8 with a dispensing device 700. The dispensing device 700 is connected to a connecting element 710 of the dispensing device 700 via a bayonet closure 720 at an end of the cartridge 200 that is axially opposite the dispensing opening 290. The connecting element 710 has an internal thread 730 which positively and/or non-positively interacts with an external thread 750 of a tappet 740 of the dispensing device 750, in order to screw the tappet 740 through the connecting element 710 into the cartridge 200 by means of a rotary movement. In order to make it easier for a user of the device 100 to screw in the tappet 740, the discharge device 700 has a handle 760. By screwing the tappet 740 into the cartridge 200, an advancement of the delivery plunger 270 in the direction of the dispensing plunger 250 is triggered. In the shown embodiment of the discharge device 700, the tappet 740 is long enough to also dispense the bone cement dough 450 provided by means of the device 100 out of the dispensing opening 290.

Figure 10:
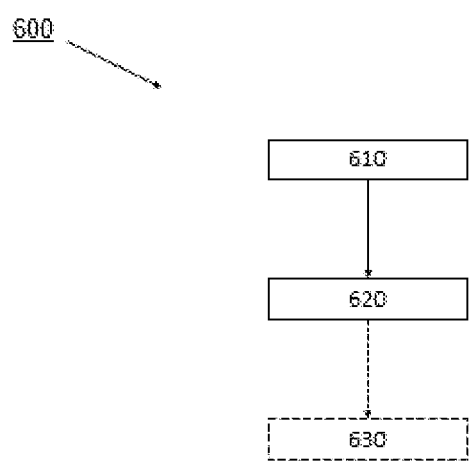

FIG. 10 shows a method 600 for providing a bone cement dough 450 from two starting components by means of the device 100 according to FIGS. 1 and 6 to 8, comprising method steps 610 and 620 and optionally 630.

In a step 610, the delivery plunger 270 is advanced in the direction of the dispensing plunger 250 into the cartridge 200. As a result of the advancement 610, the pouches 300 are pressed against the opening means 500 and, as a result, are opened reliably and concertedly, substantially simultaneously, in particular by piercing, cutting open, or tearing open. The monomer liquid 350 and the gas stored in the unopened pouches 300 can escape from the opened pouches 300a into the distal part 230 of the interior space 210.

After the pouches 300 have been opened, the monomer liquid 350 and gas are stored in the distal part 230 of the interior space 210.

In order to provide a bone cement dough 450 with as few gas bubbles as possible, the device 100 is preferably held in such a way that the dispensing plunger 250 is arranged spatially above the delivery plunger 270. From the distal part 230 of the interior space 210, gas present there, such as, for example, air or a protective gas, in particular nitrogen or argon, is delivered via the conduit means 260 into the proximal part 220 of the interior space 210, before the monomer liquid 350 is delivered in a step 620 by the conduit means 260 to form the bone cement dough 450. In this way, gas inclusions in the bone cement powder 400 are displaced by the monomer liquid 350, and no further gas is introduced after the beginning of the formation of the bone cement dough 450.

In an optional step 630, the provided bone cement dough 450 is discharged through the dispensing opening 290 in the proximal part 220 of the interior space 210 by continued advancement of the delivery plunger 270 out of the device 100. To this end, the delivery plunger 270 overcomes a force holding the dispensing plunger 250, so that delivery plunger 270 and dispensing plunger 250 are displaced together in the direction of the dispensing opening 290 within the interior space 210 and the bone cement dough 450 is dispensed.

As a result, the pouch 300 is opened, the monomer liquid 350 is delivered 620 into the proximal part 220 of the interior space 210, and optionally the provided bone cement dough 450 is dispensed 630 with a unidirectional linear movement of the delivery plunger 270 in the interior space 210 of the cartridge 200.

The advancement 610 of the delivery plunger 270 can occur via a manual application of force by a user of the device 100. In a preferred embodiment of the method 600, the device 100 is inserted into a dispensing device 700 for advancement 610, and the delivery plunger 270 is advanced by actuating the discharge device 700, for example an applicator gun. This makes it easier for the user to use the device 100.

REFERENCE SIGNS

100 Device
200 Hollow cylindrical cartridge
210 Interior space of the cartridge
220 Proximal part of the interior space
230 Distal part of the interior space
250 Dispensing plunger
251 Longitudinal axis of the dispensing plunger 252 Sealing rings of the dispensing plunger
255 Distal side of the dispensing plunger
260 Conduit means
265 Porous disk
266 Inner feedthroughs
267 Outer feedthroughs
270 Delivery plunger
275 Sealing rings of the delivery plunger
280 Groove
281 Inner groove
282 Outer groove
290 Dispensing opening
291 Closure cap
295 Plug
300 Pouches
300a Opened pouch
350 Monomer liquid
400 Bone cement powder
450 Bone cement dough
500 Opening means
510 Inner opening means
520 Outer opening means
600 Method for providing a bone cement dough
610 Advancement
620 Delivery
630 Dispensing
700 Dispensing device
710 Connecting element
720 Bayonet closure
730 Internal thread
740 Tappet
750 External thread
760 Handle

What is claimed is:

1. A device for providing a bone cement dough from two starting components, comprising:
    a hollow cylindrical cartridge with an interior space, wherein
    a bone cement powder as a first starting component is stored in a proximal part of the interior space, and at least two pouches containing a monomer liquid as a second starting component are stored in a distal part of the interior space,
    wherein a dispensing plunger axially movable in the interior space is arranged between the bone cement powder and the at least two pouches, and a delivery plunger axially movable in the interior space is arranged on a side of the at least two pouches that is axially opposite the dispensing plunger,
wherein the proximal part and the distal part of the interior space are fluidically connected to one another via a conduit means,
    wherein
    the dispensing plunger can be subdivided into four equal-sized quadrants on a distal side of the dispensing plunger facing toward the at least two pouches,
    wherein each of the four quadrants has at least one opening means so that, by advancing the delivery plunger in a direction of the dispensing plunger, the at least two pouches are to be opened by the opening means and the monomer liquid is to be delivered into the bone cement powder.

2. The device according to claim 1, wherein the opening means comprise a tip and/or a cutting edge to open the pouches.

3. The device according to claim 1, wherein the opening means are spaced apart from a longitudinal axis of the dispensing plunger at a distance in a range of one-fifth up to four-fifths of a radius of the distal side of the dispensing plunger.

4. The device according to claim 3, wherein the opening means in each quadrant comprise at least one inner opening means and at least one outer opening means, wherein the respective inner opening means and the respective outer opening means are, in each quadrant, arranged concentrically about the longitudinal axis of the dispensing plunger.

5. The device according to claim 1, wherein the opening means comprise a metal or a polymer.

6. The device according to claim 1, wherein the conduit means in each quadrant comprises at least one fluid-conducting feedthrough axially extending through the dispensing plunger to fluidically connect the proximal part and the distal part of the interior space.

7. The device according to claim 6, wherein the feedthroughs on the distal side of the dispensing plunger open into a groove extending in the distal side of the dispensing plunger, which groove fluidically connects the feedthroughs to one another.

8. The device according to claim 6, wherein the feedthroughs in each quadrant comprise at least one inner feedthrough and one outer feedthrough, wherein the inner feedthroughs open into an inner groove extending in the distal side of the dispensing plunger and the outer feedthroughs open into an outer groove extending in the distal side of the dispensing plunger, wherein the inner groove fluidically connects the inner feedthroughs to one another and the outer groove fluidically connects the outer feedthroughs to one another.

9. The device according to claim 8, wherein the inner groove and the outer groove are fluidically connected to one another via a connecting groove extending in the distal side of the dispensing plunger.

10. The device according to claim 1, wherein the delivery plunger has a receptacle on a proximal side of the device facing toward the dispensing plunger, in order to receive the opening means upon the delivery plunger being advanced in the direction of the dispensing plunger.

11. The device according to claim 10, wherein the receptacle comprises recesses.

12. The device according to claim 10, wherein the receptacle comprises an elastomer layer.

13. A method for providing the bone cement dough from the two starting components by the device according to claim 1, comprising the following steps:
    a. advancing the delivery plunger in the direction of the dispensing plunger to open the at least two pouches by the opening means,
    b. delivering the monomer liquid into the proximal part of the interior space to form the bone cement dough.

14. The method of claim 13, wherein the device is inserted into a dispensing device for advancement of the delivery plunger.

15. The method according to claim 13, wherein the monomer liquid is distributed with an aid of a hydrophilic additive in the bone cement powder.

* * * * *